(12) United States Patent
Lee

(10) Patent No.: US 7,588,934 B2
(45) Date of Patent: Sep. 15, 2009

(54) GENE ENCODING FUMARATE HYDRATASE C AND USE THEREOF

(75) Inventor: Sang Yup Lee, Daejeon (KR)

(73) Assignee: Korea Advanced Insitute of Science and Technology (KR)

( * ) Notice: Subject to any disclaimer, the term of this patent is extended or adjusted under 35 U.S.C. 154(b) by 153 days.

(21) Appl. No.: 11/228,927

(22) Filed: Sep. 16, 2005

(65) Prior Publication Data

US 2007/0042477 A1   Feb. 22, 2007

(30) Foreign Application Priority Data

Aug. 19, 2005   (KR) .................. 10-2005-0076317

(51) Int. Cl.
*C12N 15/00* (2006.01)
*C12N 15/09* (2006.01)
*C12N 15/63* (2006.01)
*C12N 15/64* (2006.01)
*C12N 15/74* (2006.01)

(52) U.S. Cl. ................. 435/320.1; 435/243; 435/252.3; 435/254.11; 435/69.1

(58) Field of Classification Search ............ None
See application file for complete search history.

(56) References Cited

U.S. PATENT DOCUMENTS 5,143,834 A    9/1992   Glassner et al.
5,168,055 A   12/1992   Datta et al.
5,504,004 A    4/1996   Guettler et al.
5,521,075 A    5/1996   Guettler et al.
5,770,435 A    6/1998   Donnelly et al.

FOREIGN PATENT DOCUMENTS

WO   WO 2005/052135 A1   9/2005

OTHER PUBLICATIONS

SCORE search resutls AE016827, downloaded Jul. 6, 2006.*
AAU37367, *fumC* protein *Mannheimia*, Oct. 19, 2004, downloaded Sep. 16, 2007.*
Zeikus et al., *Appl. Microbiol. Biotechnol.*, 51:545, 1999.
Willke et al., *Appl. Microbiol. Biotechnol.*, 66:131, 2004.
Hong et al., *Biotechnol. Lett.*, 22:871, 2000.
Laivenieks et al., *Appl. Environ. Microbiol.*, 63:2273, 1997.
Hong et al., *Nature Biotechnol.*, 22:1275, 2004.
Kehrenberg et al., *J. Antimicrob. Chemother.*, 49:383, 2002.
Gray et al., *Biochim. Biophys. Acta*, 117:33, 1966.

\* cited by examiner

*Primary Examiner*—Maria B Marvich
(74) *Attorney, Agent, or Firm*—Steven J. Hultquist; Kelly K. Reynolds; Intellectual Property/Technology Law

(57) ABSTRACT

A nucleotide sequence encoding a fumarate hydratase C and a method for preparing succinic acid using the same, more particularly, a fumarate hydratase C having the activity of converting malate to fumarate, a fumC nucleotide sequence encoding the fumarate hydratase C, a recombinant vector containing the nucleotide sequence, a microorganism transformed with the recombinant vector, and a method for preparing succinic acid using the transformed microorganism.

7 Claims, 3 Drawing Sheets

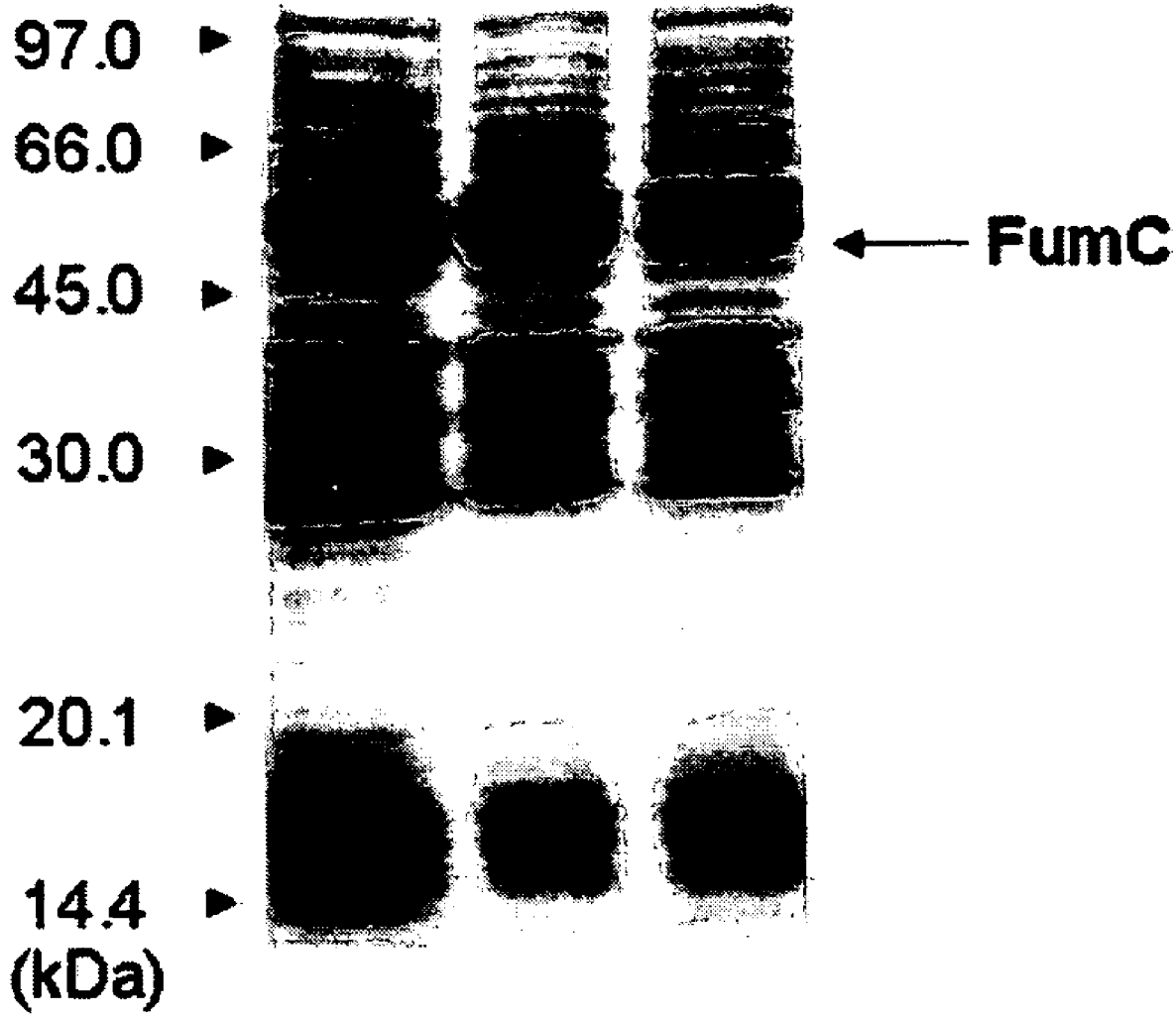

GENE ENCODING FUMARATE HYDRATASE C AND USE THEREOF

CROSS-REFERENCE TO RELATED APPLICATION

Priority is hereby claimed under 35 USC 119 of Korean Patent Application No. 10-2005-0076317 filed on Aug. 19, 2005 in the Korean Intellectual Property Office. The disclosure of said Korean Patent Application is hereby incorporated herein by reference in its entirety.

BACKGROUND OF THE INVENTION

1. Field of the Invention

The present invention relates to a novel gene encoding a fumarate hydratase C and a method for preparing succinic acid using the same, more particularly, to a fumarate hydratase C having the activity of converting malate to fumarate, a novel fumC gene encoding the fumarate hydratase C, a recombinant vector containing the gene, a microorganism transformed with the recombinant vector, and a method for preparing succinic acid using the transformed microorganism.

2. Background of the Related Art

Succinic acid, which is a dicarboxylic acid ($HOOCCH_2CH_2COOH$) with four carbon atoms initially purified from amber resin, is used in a very wide range of industrial applications (Zeikus et al., Appl. Microbiol. Biotechnol., 51:545, 1999). Particularly, as the utility of succinic acid as a main raw material of biodegradable polymers was recently proven, a rapid increase in the demand of succinic acid is expected (Willke et al., Appl. Microbiol. Biotechnol., 66:131, 2004).

Succinic acid can be produced by chemical synthesis and fermentation. Most commercially available succinic acid recently has been produced from n-butane as a starting material derived from LNG or crude petroleum, by chemical manufacturers such as BASF, DuPont and BP Chemicals. Chemical processes for the synthesis of succinic acid have the problem that they cause the discharge of large amounts of harmful solid wastes, waste solutions and waste gases (including carbon monoxide) during the preparation of succinic acid, and particularly, have the limitation that they use fossil raw material as a basic material. Only a small amount of succinic acid, which is used in special applications, such as medical drugs, is currently produced by traditional microbial processes.

In an attempt to solve the described problems occurring in the chemical processes for the synthesis of succinic acid, studies on the production of succinic acid by fermentation processes have been conducted by many researchers. The method for the production of succinic acid by fermentation is a method of producing succinic acid from renewable raw materials using microorganisms. Bacterial strains that are used in the production of succinic acid can be broadly divided into recombinant E. coli and ruminal bacteria, such as Actinobacillus, Anaerobiospirillum, Bacteroides, Mannheimia, Succinimonas, Succinivibrio, etc.

A research team of the University of Chicago has attempted to increase the production of succinic acid by preparing a mutant strain AFP111 (ATCC No. 202021) in which E. coli ldh and pfl genes involved in the production of lactic acid and formic acid have been removed and a ptsG gene of the glucose transfer system has been manipulated (U.S. Pat. No. 5,770,435).

Among ruminal bacteria, Actinobacillus, Anaerobiospirillum and Mannheimia strains have been relatively much-studied. Michigan Biotechnology Institute (MBI) has developed an Actinobacillus succinogenes 130Z strain (ATCC No. 55618) and a process for producing a high concentration of succinic acid using the same (U.S. Pat. No. 5,504,004). Also, such institute has developed Anaerobiospirillum succiniciproducens and its mutant strains, and a process for the production and purification of succinic acid (U.S. Pat. Nos. 5,521,075; 5,168,055; and 5,143,834).

However, the processes for preparing succinic acid using the described strains have low productivity and result in the production of large amounts of byproducts in addition to succinic acid, thus requiring high costs for the separation and purification of succinic acid. Accordingly, there has been an urgent need for the development of a bacterial system that has high productivity and at the same time, can inhibit the production of byproducts (Hong et al., Biotechnol. Lett., 22:871, 2000).

For this purpose, the isolation of an excellent succinic acid-producing bacterial strain, the establishment of genome sequences and the understanding of metabolic characteristics of bacterial strains based on them are first required. With such basis, it then is necessary to secure gene manipulation technologies required for the construction of a novel gene recombinant bacterial strain. Although there has been a prior attempt to increase the production of succinic acid using the phosphoenolpyruvate carboxykinase (pckA) gene of Anaerobiospirillum succiniciproducens (Laivenieks et al., Appl. Environ. Microbiol., 63:2273, 1997), the art has failed to develop a gene recombinant strain based on the full genome sequence of ruminal bacteria.

Meanwhile, the present inventors previously isolated a Mannheimia succiniciproducens MBEL55E strain from the rumen of a Korean cow that produces succinic acid in high efficiency using various substrates, and reported the full genome sequence of the strain (Hong et al., Nature Biotechnol., 22:1275, 2004). Particularly, the above strain is characterized by immobilizing carbon dioxide, known as a greenhouse gas, in the synthesis of succinic acid. Also, this applicant previously prepared succinic acid with high yield by deleting a lactic acid dehydrogenase gene (ldhA) and a pyruvate formate-lyase (pfl) from Mannheimia succiniciproducens MBEL55E, so as to construct mutant strain Mannheimia sp. LPK (KCTC 10558BP), and deleting a phosphotransacetylase gene (pta) and an acetate kinase gene (ackA) from the LPK strain to construct mutant strains Mannheimia sp. LPK7, and then culturing the resulting mutant strain in an anaerobic condition (WO 05/052135 A1). However, the mutant strain has a problem that it results in the accumulation of malate to a certain degree as a byproduct during the culture thereof.

Accordingly, there continues to be an urgent need in the art for the development of a bacterial system for high productivity, low byproduct succinic acid production that overcomes the deficiencies of the prior art.

SUMMARY OF THE INVENTION

The present invention relates to a novel gene(fumC) encoding fumarate hydratase C derived from Mannheimia succiniciproducens MBEL55E that is usefully employed in the production of succinic acid.

The present invention relates in one aspect to a recombinant vector containing said gene, and to a recombinant microorganism transformed with said recombinant vector.

Still another aspect of the present invention relates to a method for preparing succinic acid using said recombinant microorganism.

In one aspect, the present invention relates to a fumarate hydratase C having an amino acid sequence of SEQ ID NO: 4, which has the activity of converting malate to fumarate, as well as a gene (fumC) encoding the fumarate hydratase C. In one preferred aspect of the present invention, said gene has a DNA sequence of SEQ ID NO: 3.

In another aspect, the present invention relates to a recombinant vector containing the fumC gene and a recombinant microorganism obtained by introducing the fumC gene or the recombinant vector into a host cell selected from the group consisting of bacteria, yeast and mold.

In a still further aspect of the present invention, the recombinant vector is preferably pMVDfumC, pMV19fumC, or pMEfumC, but is not limited thereto. Additionally, the host cell is a succinic acid-producing microorganism. The succinic acid-producing microorganism is the genus *Mannheimia* microorganism, and preferably, the genus *Mannheimia* microorganism in which one or more pathways selected from the group consisting of an acetate-producing pathway, a lactate-producing pathway, a formate-producing pathway, an ethanol-producing pathway and an oxaloacetate-producing pathway, were blocked. More preferably, the succinic acid-producing microorganism is a *Mannheimia* sp. LPK (KCTC 10558BP) or LPK7.

As shown in a succinate synthesis pathway described more fully hereinafter with reference to FIG. 1, the fumC gene can convert malate to fumarate. Thus, when the fumC gene is overexpressed, it is possible to increase the production of fumarate and succinic acid, as well as to minimize the production of malate as a byproduct.

Accordingly, the present invention relates in another aspect to a method for preparing succinic acid, the method including the steps of: culturing the recombinant microorganism; and recovering succinic acid from the culture broth of the recombinant microorganism. The steps of culturing the recombinant microorganism and recovering the succinic acid can be carried out by the culture method and the isolation and purification method of succinic acid, which are generally known in the prior fermentation industry.

In still another aspect, the present invention relates to a method for preparing fumarate, the method including converting malate to fumarate in the presence of fumarate hydratase C.

The fumarate hydratase used in the present invention is named as a fumarase used generally, and has the same function as the fumarase.

Other aspects, features and embodiments of the present invention will be more fully apparent from the following detailed description and appended claims.

BRIEF DESCRIPTION OF THE DRAWINGS

FIG. 3 is an SDS-PAGE showing the protein expression of recombinant *Mannheimia* LPK7pMEfumC containing recombinant plasmid pMEfumC.

DETAILED DESCRIPTION OF THE PREFERRED EMBODIMENT

The present invention is based on the discovery of a bacterial system for high productivity, low byproduct succinic acid production that overcomes the deficiencies of the prior art.

Figure 1:
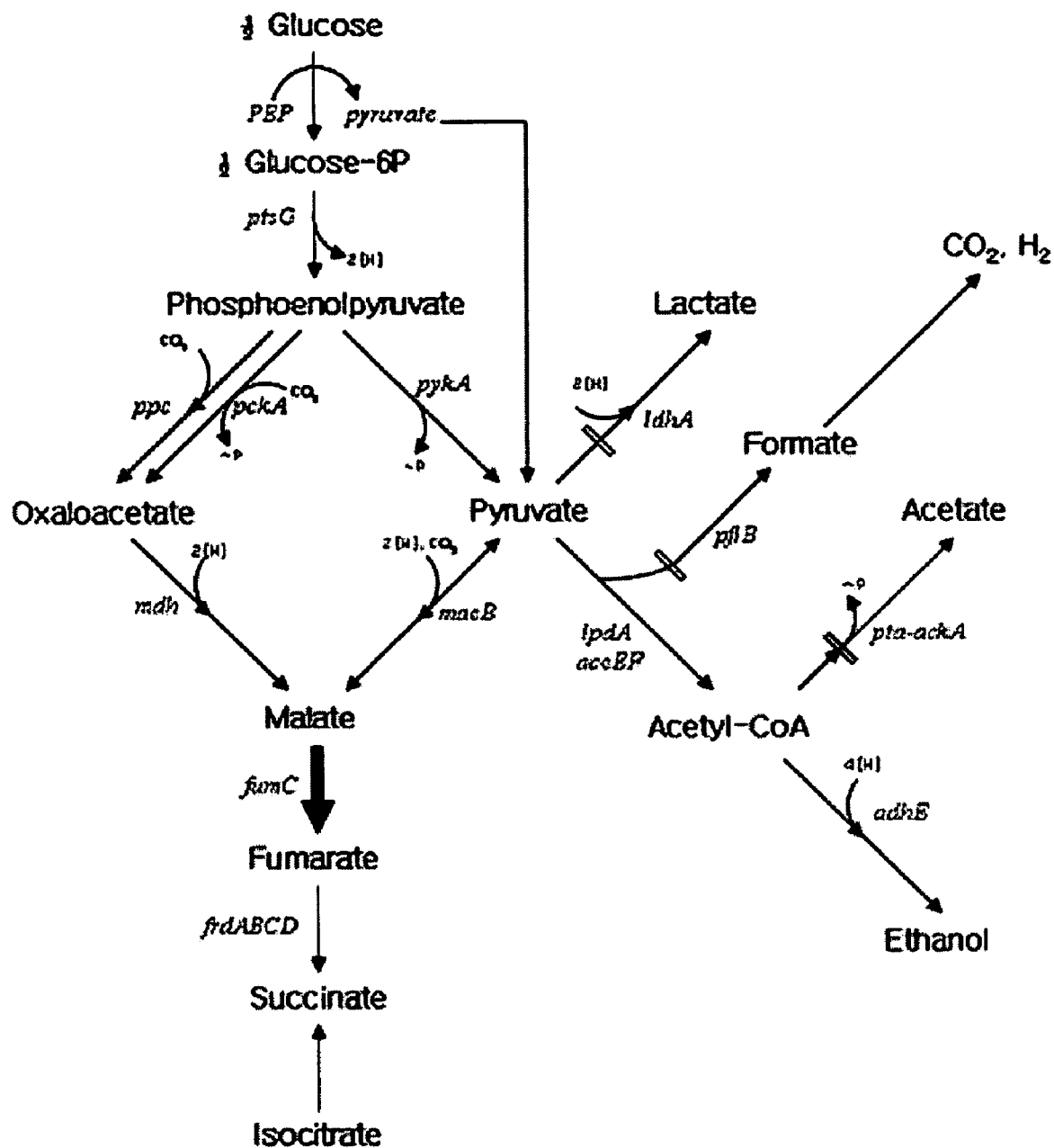
FIG. 1 is a schematic diagram showing a pathway for the synthesis of succinic acid from *Mannheimia* strain.

The present inventors have made extensive efforts to find the core gene involved in succinic acid metabolism in order to develop a microbial strain capable of minimizing the production of malate and of producing succinic acid with higher yield, on the basis of a succinic acid synthetic pathway shown in FIG. 1, and as a result, they have cloned a fumarate hydratase C-encoding gene (fumC) derived from *Mannheimia succiniciproducens* MBEL55E and determined the function thereof, thereby completing the present invention.

The present invention is more fully described hereinafter and with reference to illustrative examples. It is to be understood, however, that these examples are presented in order to more fully describe the present invention, and are correspondingly not intended to be construed to limit the present invention.

Although only the use of the specified expression vector and the genus *Mannheimia* microorganism which is a succinic acid-producing microorganism, as a host cell, to express the inventive gene, is illustrated in the following examples, the use of other kinds of expression vectors and host cells will be readily apparent to those skilled in the art.

EXAMPLE 1

Preparation of *Mannheimia/E. coli* Shuttle Vector pME

*Mannheimia/E. coli* shuttle vector pME was prepared from pMVSCS1 reported to be isolated from *Mannheimia* (Kehrenberg et al., *J Antimicrob. Chemother.*, 49:383, 2002) and *E. coli* expression vector pKK223-3 (Amersham Pharmacia Biotech). For this purpose, pKK223-3 was partially digested with BamHI and AccI to collect a 2.7kb fragment containing pBR322 ori and an ampicillin-resistant gene, and the single strand portions are filled with T4 DNA polymerase to make blunt ends. The blunt ends are ligated to prepare pKKD (2.7kb). pMVSCS1 (5.6kb) was digested with XhoII, and ligated with pKKD digested with restriction enzyme BamHI to prepare fusion vector pMVD (8.3kb). The pMVD was digested with NcoI, and a 5.9kb fragment was religated to construct *Mannheimia/E. coli* shuttle vector pME.

EXAMPLE 2

Identification of novel gene (fumC) derived from *Mannheimia succiniciproducens* MBEL55E and preparation of a recombinant plasmid introduced with fumC gene A fumarate hydratase C-encoding gene (fumC) of SEQ ID NO: 3 derived from *Mannheimia succiniciproducens* MBEL55E (KCTC 0769BP) was cloned, including a promoter and a transcription termination sequence.

Figure 2:
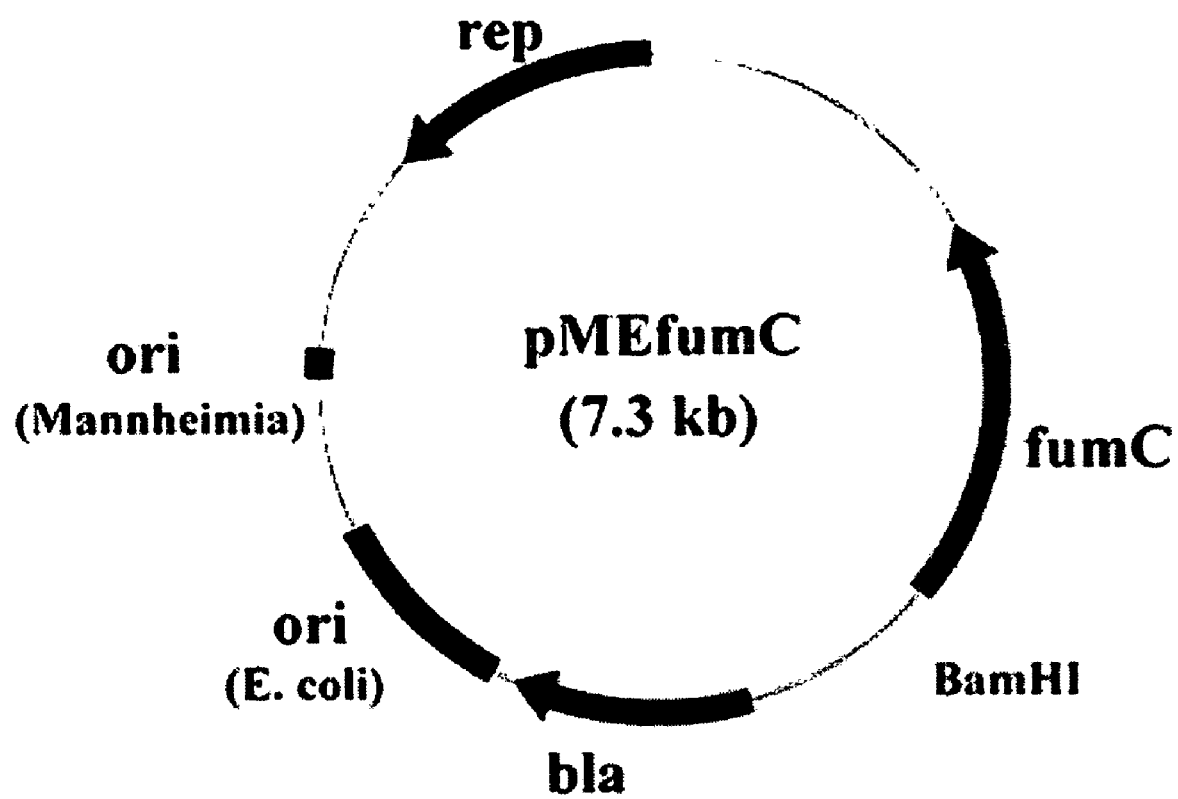
FIG. 2 is a gene map of recombinant plasmid pMEfumC.

For this purpose, the chromosome of *Mannheimia succiniciproducens* MBEL55E as a template was subjected to PCR with primers of SEQ ID NOs: 1 and 2, under conditions shown in Table 1 below. The resulting fumC gene was digested with restriction enzyme BamHI and restricted at the sites of ClaI and BamHI restriction enzymes in *Mannheimia/E. coli* shuttle vector pME and inserted with T4 DNA polymerase in the end region to construct plasmid pMEfumC by ligation (FIG. 2). In this way, a fumarate hydratase C-encoding gene (fumC) derived from *Mannheimia succiniciproducens* MBEL55E was cloned.

TABLE 1

Conditions for amplification of fumC gene.

| Gene | Primer | Restriction enzyme site contained in the primer | Reaction condition |
|---|---|---|---|
| fumC | fumC-F (SEQ ID NO: 1), fumC-R (SEQ ID NO: 2) | BamHI | Cycle I: 94° C., 5 min<br>Cycle II: (30 cycles)<br>94° C., 40 sec<br>65° C., 30 sec<br>72° C., 3 min<br>Cycle III: 72° C., 5 min<br>Cycle IV: 4° C., forever |

The DNA sequence of the cloned fumC of *Mannheimia succiniciproducens* MBEL55E was analyzed and the amino acid sequence of fumarate hydratase C was inferred therefrom. As a result, the fumC gene of *Mannheimia succiniciproducens* MBEL55E had a DNA sequence of 1,395 bp (SEQ ID NO: 3), and the fumarate hydratase C consisted of 465 amino acid residues (SEQ ID NO: 4).

The homology of the fumC DNA sequence derived from *Mannheimia succiniciproducens* MBEL55E was analyzed, and as a result, this gene showed the highest homology of 82% (score: 565) with the fumC of *Haemophilus influenza* 86-028NP, a homology of 81% (score: 535) with the fumC of *Haemophilus influenza* Rd KW20, and a homology of 82% (score: 375) with the fumC of *Pasteurella multocida* subsp. multocida Pm70. The G+C amount of the *Mannheimia succiniciproducens* MBEL55E fumC was found to be 43.8% which is slightly higher than 39.1% for a *Haemophilus influenza* 86-028NP fumC gene and 40.9% for an *Pasteurella multocida* Pm70 fumC gene.

Meanwhile, the frequency of using amino acid codons in the *Mannheimia succiniciproducens* MBEL55E fumC gene was examined and the results are shown in Table 2 below. As shown in Table 2 below, the frequency of using amino acid codons in the fumC gene showed a different result from that in generally known *E. coli*. For example, for the frequency of using lysine codons, AAA was used at a high frequency of 100% in the *Mannheimia succiniciproducens* MBEL55E fumC gene, but AAA and AAG were used at frequencies of 76% and 24%, respectively in generally known *E. coil*. For the frequency of using glutamate codons, GAA was used at a frequency of 96% in the *Mannheimia succiniciproducens* MBEL55E fumC gene, but GAA and GAG in *E. coli* were used at frequencies of 96% and 30%, respectively. Also, for the frequency of using glutamine codons, CAA and CAG were used at frequencies of 84% and 16%, respectively in the *Mannheimia succiniciproducens* MBEL55E fumC gene, but at frequencies of 31% and 69%, respectively in *E. coli*.

TABLE 2

Frequency of using amino acid codons

| Amino acid | Codon | Frequency of use in MBEL55E fumC | Average frequency of use in *E. coli* |
|---|---|---|---|
| Ala | GCA | 0.36 | 0.22 |
|  | GCC | 0.21 | 0.25 |
|  | GCG | 0.29 | 0.34 |
|  | GCT | 0.14 | 0.19 |
| Arg | AGA | — | 0.04 |
|  | AGG | — | 0.03 |
|  | CGA | — | 0.05 |
|  | CGC | 0.31 | 0.37 |
|  | CGG | — | 0.08 |
|  | CGT | 0.69 | 0.42 |
| Asn | AAC | 0.60 | 0.61 |
|  | AAT | — | 0.39 |
|  | GAC | — | 0.41 |
|  | GAT | 0.40 | 0.59 |
| Cys | TGC | 0.50 | 0.57 |
|  | TGT | 0.50 | 0.43 |
| STOP | TAA | — | 0.62 |
|  | TAG | — | 0.09 |
|  | TGA | — | 0.30 |
| Gln | CAA | 0.84 | 0.31 |
|  | CAG | 0.16 | 0.69 |
| Glu | GAA | 0.96 | 0.70 |
|  | GAG | 0.04 | 0.30 |
| Gly | GGA | 0.03 | 0.09 |
|  | GGC | 0.26 | 0.40 |
|  | GGG | — | 0.13 |
|  | GGT | 0.71 | 0.38 |
| His | CAC | 0.46 | 0.48 |
|  | CAT | 0.54 | 0.52 |
| Ile | ATA | — | 0.07 |
|  | ATC | — | 0.46 |
|  | ATT | — | 0.47 |
| Leu | CTA | 0.05 | 0.03 |
|  | CTC | — | 0.10 |
|  | CTG | 0.05 | 0.55 |
|  | CTT | 0.03 | 0.10 |
|  | TTA | 0.68 | 0.11 |
|  | TTG | 0.20 | 0.11 |
| Lys | AAA | 1.00 | 0.76 |
|  | AAG | — | 0.24 |
| Met | ATG | 0.67 | 1.00 |
| Phe | TTC | 0.33 | 0.49 |
|  | TTT | — | 0.51 |
| Pro | CCA | 0.10 | 0.20 |
|  | CCC | — | 0.10 |
|  | CCG | 0.62 | 0.55 |
|  | CCT | 0.29 | 0.16 |
| Ser | AGC | 0.17 | 0.27 |
|  | AGT | — | 0.13 |
|  | TCA | 0.39 | 0.12 |
|  | TCC | 0.13 | 0.17 |
|  | TCG | 0.09 | 0.13 |
|  | TCT | 0.22 | 0.19 |
| Thr | ACA | 0.21 | 0.12 |
|  | ACC | 0.48 | 0.43 |
|  | ACG | 0.06 | 0.23 |
|  | ACT | 0.24 | 0.21 |
| Trp | TGG | 1.00 | 1.00 |
| Tyr | TAG | 0.25 | 0.47 |
|  | TAT | 0.75 | 0.53 |
| Val | GTA | 0.33 | 0.17 |
|  | GTC | — | 0.20 |
|  | GTG | 0.30 | 0.34 |
|  | GTT | 0.37 | 0.29 |

EXAMPLE 3

Production of Succinic Acid by Use of Transformed *Mannheimia*

The recombinant plasmid pMEfumC constructed in Example 2 was transformed into *Mannheimia* LPK7 (KCTC 10626BP) by electroporation to prepare LPK7pMEfumC. Also, pME was introduced into *Mannheimia* LPK7 (KCTC 10626BP) to prepare LPK7pME.

Each of the prepared recombinant strains was inoculated in 10 ml of a complex medium containing 9 g/l of glucose and cultured in an anaerobic condition at 39° C. for 16 hours. Each of the cultured strains was transferred in 250 ml of a complex medium containing 9 g/l of glucose and further cultured in the medium at 39° C. At this time, 100 µg/l of ampicillin as an antibiotic was added. The fermentation of each of the strains was performed by inoculating 250 ml of the *Mannheimia* culture broth in 2.5 L of a complex medium, and the fermentation conditions were as follows: initial glucose concentration: 20 g/l, pH: 6.8, and culture temperature: 39° C. For the adjustment of pH during the fermentation, ammonia solution (28%, v/v) was used, and the concentration of antibiotic ampicillin was the same as described above. A sample from each of the recombinant *Mannheimia* strains was collected during the fermentation, and the collected sample was centrifuged at 13,000 rpm and 4° C. for 10 minutes, and the concentrations of metabolites and succinic acid in the supernatant were analyzed by high-performance liquid chromatography (HPLC). The results are shown in Table 3 below.

As shown in Table 3, in the case where the recombinant plasmid pMEfumC containing the fumC gene of MBEL55E was introduced into the recombinant *Mannheimia* LPK7, the concentration of malate was reduced. These results suggest that the fumC gene of MBEL55E encodes an enzyme involved in the conversion of malate to fumarate during several steps of the succinic acid-producing pathway. The reduction rate of malate in LPK7 was 151%, which is much higher than that in the established research.

The enzyme activity of the cell extracts was measured with a spectrophotometer, in which the cell extract was allowed to react by adding a reaction buffer (0.1 M Hepes-KOH buffer (pH 8.0), 50 mM L-malate) to a 1 cm-width cuvette and adding the cell extract to the reaction buffer to a final volume of 1 ml, and the fumarate at 240 nm was measured. The results are shown in Table 4.

As shown in Table 4, the LPK7pMEfumC cell extract showed 282% increase in the activity of fumarate hydratase C compared to the LPK7pME cell extract. This result confirms that the fumC gene according to the present invention is a gene encoding fumarate hydratase C having the activity of converting malate to fumarate.

TABLE 4

Enzyme activity of transformed *Mannheimia* strains

| Strain | Plasmid | *Enzyme activity (U) | Enzyme activity increase rate(%) |
|---|---|---|---|
| LPK7 | pME | 186.7 | 100 |
| LPK7 | pMEfumC | 526.6 | 282 |

*Enzyme activity shows the titer of fumarate hydratase C contained in 1 mg of total protein. An enzyme activity of 1.0 U is defined as the amount of enzyme required for converting 1 nmole of a substrate to a certain product at 37° C. for 1 minute.

The activity of the fumarate hydratase C according to the present invention was compared to the known enzyme, and the result is shown in Table 5 below. As shown in Table 5, the fumarate hydratase C of the *Mannheimia* strain transformed with the inventive fumC gene showed much higher activity

TABLE 3

Concentration of malate in fermentation of transformed *Mannheimia*

| Strain | Plasmid | Fermentation time (hrs.) | Cell concentration (OD$_{600}$) | Malate concentration (g/l) | Malate reduction rate (%) | Succinic acid concentration (g/l) |
|---|---|---|---|---|---|---|
| LPK7 | pME | 25 | 3.08 | 2.58 | 100 | 12.98 |
| LPK7 | pMEfumC | 50 | 2.22 | 1.26 | 151 | 12.47 |

Meanwhile, each of the strains was analyzed by SDS-PAGE, and the results are shown in FIG. 3. As can be seen in FIG. 3, the recombinant *Mannheimia* LPK7pMEfumC transformed with the recombinant plasmid pMEfumC showed a remarkable increase in the expression of fumarate hydratase C as compared to the recombinant *Mannheimia* LPKpME (control group) transformed with pME.

EXAMPLE 4

Measurement of Fumarate Hydratase C Activity by Use of Transformed *Mannheimia*

The culture broth of *Mannheimia* LPK7pMEfumC prepared in Example 3 was centrifuged at 13,000 rpm and 4° C. for 5 minutes. The precipitated cells were washed 2 times with an iced buffer solution (100 mM Tris-HCl (pH 7.0), 20 mM KCl, 5 mM MnSO$_4$, 2 mM DTT, 0.1 mM EDTA), and the washed cells were suspended in the same buffer and the cell membranes were disrupted by sonication. The cell debris was removed by a centrifugation, and the cell extract supernatant was used for the measurement of enzyme activity.

than the fumarate hydratase of *E. coli* K12 (Gray et al., *Biochim. Biophys. Acta*, 117:33, 1966).

TABLE 5

Comparison of fumarate hydratase activities between transformed *Mannheimia* and *E. coli*

| Strain | Enzyme activity (U) | Gene homology (%) |
|---|---|---|
| LPK7pMEmaeB | 526.7 | 62.5 |
| *E. coli* K12 | 160 | |

As described and proven in detail above, the present invention provides a novel gene (fumC) encoding fumarate hydratase C. The nucleotide sequence of the fumC gene may be a DNA sequence of SEQ ID NO: 3, or a sequence having appropriate homology thereto (e.g., that is at least 85%, and more preferably is at least 90, 91, 92, 93, 94, 95, 96, 97, 98, or 99% homologous to the nucleotide sequence of SEQ ID NO: 3). The novel gene according to the present invention is useful to prepare a recombinant microorganism capable of effectively reducing malate produced as a byproduct in the production of succinic acid. Also, the fumarate hydratase C according to the present invention is useful to prepare fumarate from malate. Thus, the fumC gene according to the present invention is useful in increasing the production of various metabolites in the operation of central metabolic pathways by the combination with a suitable metabolic pathway.

While the present invention has been described in detail with reference to specific features, it will be apparent to those skilled in the art that this description is illustrative only of one preferred embodiment and is not intended in any way to limit the scope of the present invention, as defined by the appended claims and equivalents thereof.

What is claimed is:

1. A recombinant vector containing an isolated fumC gene encoding a fumarate hydratase C having the amino acid sequence of SEQ ID NO: 4 and having the activity of converting malate to fumarate.

2. A recombinant microorganism obtained by introducing an isolated fumC gene encoding a fumarate hydratase C having the amino acid sequence of SEQ ID NO: 4 and having the activity of converting malate to fumarate, or obtained by introducing the recombinant vector according to claim 1; into a host cell selected from the group consisting of a bacterial cell, a yeast cell, and a mold cell.

3. The recombinant microorganism according to claim 2, wherein the host cell comprises a succinic acid-producing pathway.

4. The recombinant microorganism according to claim 3, wherein the host cell is from the genus *Mannheimia*.

5. The recombinant microorganism according to claim 4, wherein the genus *Mannheimia* comprises *Mannheimia* sp. LPK and *Mannheimia* LPK7.

6. The recombinant microorganism according to claim 3 wherein the host cell comprises one or more additional pathways, selected from the group consisting of an acetate-producing pathway, a lactate-producing pathway, a formate-producing pathway, an ethanol-producing pathway and an oxaloacetate-producing pathway, blocked.

7. A method of producing succinic acid, the method comprising the steps of culturing a recombinant microorganism comprising a recombinant vector containing an isolated fumC gene encoding a fumarate hydratase C having the amino acid sequence of SEQ ID NO: 4 and having the activity of converting malate to fumarate wherein the fumC gene is operably linked to expression control sequences;

and recovering succinic acid from the culture broth of the recombinant microorganism.

* * * * *

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Synthetic Construct

<400> SEQUENCE: 1
cgggatccac aaaagaaaag tctgctatc                                    29

<210> SEQ ID NO 2
<211> LENGTH: 28
<212> TYPE: DNA
<213> ORGANISM: Artificial Sequence
<220> FEATURE:
<223> OTHER INFORMATION: Synthetic Construct

<400> SEQUENCE: 2
cgggatccca tccgctgcgg ttttgtaa                                     28

<210> SEQ ID NO 3
<211> LENGTH: 1395
<212> TYPE: DNA
<213> ORGANISM: Mannheimia succiniciproducens MBEL55E

<400> SEQUENCE: 3
atgacagcgt tcgtattga aaaagatact atgggtgaag tgcaggttcc tgcagataaa      60
tactgggcgg cacaaaccga acgttctcgc aataatttta aaattggtcc tgcggcatct    120
atgccacatg aaatcattga agcattcggt tatttgaaaa aagccgctgc ttttgcaaat    180
acagatttag gtgttttacc tgccgaaaaa cgcgatttaa tcggtcaggc ttgtgatgaa    240
attcttgccc gtaaattaga cgaccaattc ccgttggtaa tctggcaaac cggttcgggt    300
acgcaatcta acatgaacct gaacgaagtt atcgctaacc gcgcccatgt gatcaacggc    360
ggaaaattag gtgaaaaatc tatcattcac ccgaatgacg atgtaaacaa atcccaatct    420
tcaaacgata cttacccgac tgcaatgcac atcgcggcat ataaaaaagt agttgaagcc    480
actattccgg cggttgagcg cttacaaaaa accttagcgg caaaagctgc agaattcaaa    540
gatgtggtga aaatcggccg tactcactta atggacgcaa caccattaac tttaggtcag    600
gaattcagcg gttatgcggc gcaattaagc tttggtttaa ctgcaattaa aaataccttaa   660 ccgcatttac gtcaattggc attaggcggt accgccgtag gtacaggttt gaatacgcct    720
aaaggttatg atgtgaaagt tgcggaatat attgcgaaat tcaccggtct tccgttcatt    780
accgcagaaa acaaatttga agctttagca acccatgatg ccattgtgga aacccacggc    840
gcgttaaaac aagttgccat gtcattattc aaaattgcta acgatattcg tttattggca    900
tccggcccgc gttcaggtat cggcgaaatc ttaattcctg aaaacgaacc gggttcgtca    960
atcatgccgg gtaaagtaaa tccgactcaa tgcgaagcca tgacaatggt tgccgcacaa   1020

```
gtgttaggta acgataccac catttcattc gcaggctcac aaggtcactt cgaactaaac    1080
gtatttaaac cggtaatggc ggcgaacttc ctgcaatccg ctcaattaat cgcggacgtt    1140
tgtatctcat tcgacgaaca ttgcgcaacc ggtattcaac cgaatacacc gcgtattcaa    1200
catttgctag acagctcatt aatgttggta accgcattaa atacccatat cggttatgaa    1260
aatgcggcga aaattgcgaa aaccgcacac aaaaacggca ccacattacg tgaagaagca    1320
atcaacttag gcttagtttc agccgaagac ttcgacaaat gggtggtacc tgccgatatg    1380
gttggtagct tgaaa                                                    1395
```

<210> SEQ ID NO 4
<211> LENGTH: 465
<212> TYPE: PRT
<213> ORGANISM: Mannheimia succiniciproducens MBEL55E

<400> SEQUENCE: 4

```
Met Thr Ala Phe Arg Ile Glu Lys Asp Thr Met Gly Glu Val Gln Val
1               5                   10                  15

Pro Ala Asp Lys Tyr Trp Ala Ala Gln Thr Glu Arg Ser Arg Asn Asn
            20                  25                  30

Phe Lys Ile Gly Pro Ala Ala Ser Met Pro His Glu Ile Ile Glu Ala
        35                  40                  45

Phe Gly Tyr Leu Lys Lys Ala Ala Ala Phe Ala Asn Thr Asp Leu Gly
    50                  55                  60

Val Leu Pro Ala Glu Lys Arg Asp Leu Ile Gly Gln Ala Cys Asp Glu
65                  70                  75                  80

Ile Leu Ala Arg Lys Leu Asp Asp Gln Phe Pro Leu Val Ile Trp Gln
                85                  90                  95

Thr Gly Ser Gly Thr Gln Ser Asn Met Asn Leu Asn Glu Val Ile Ala
            100                 105                 110

Asn Arg Ala His Val Ile Asn Gly Gly Lys Leu Gly Glu Lys Ser Ile
        115                 120                 125

Ile His Pro Asn Asp Asp Val Asn Lys Ser Gln Ser Ser Asn Asp Thr
    130                 135                 140

Tyr Pro Thr Ala Met His Ile Ala Ala Tyr Lys Lys Val Val Glu Ala
145                 150                 155                 160

Thr Ile Pro Ala Val Glu Arg Leu Gln Lys Thr Leu Ala Ala Lys Ala
                165                 170                 175

Ala Glu Phe Lys Asp Val Val Lys Ile Gly Arg Thr His Leu Met Asp
            180                 185                 190

Ala Thr Pro Leu Thr Leu Gly Gln Glu Phe Ser Gly Tyr Ala Ala Gln
        195                 200                 205

Leu Ser Phe Gly Leu Thr Ala Ile Lys Asn Thr Leu Pro His Leu Arg
    210                 215                 220

Gln Leu Ala Leu Gly Gly Thr Ala Val Gly Thr Gly Leu Asn Thr Pro
225                 230                 235                 240

Lys Gly Tyr Asp Val Lys Val Ala Glu Tyr Ile Ala Lys Phe Thr Gly
                245                 250                 255

Leu Pro Phe Ile Thr Ala Glu Asn Lys Phe Glu Ala Leu Ala Thr His
            260                 265                 270

Asp Ala Ile Val Glu Thr His Gly Ala Leu Lys Gln Val Ala Met Ser
        275                 280                 285

Leu Phe Lys Ile Ala Asn Asp Ile Arg Leu Leu Ala Ser Gly Pro Arg
    290                 295                 300
```

-continued

```
Ser Gly Ile Gly Glu Ile Leu Ile Pro Glu Asn Glu Pro Gly Ser Ser
305                 310                 315                 320

Ile Met Pro Gly Lys Val Asn Pro Thr Gln Cys Glu Ala Met Thr Met
            325                 330                 335

Val Ala Ala Gln Val Leu Gly Asn Asp Thr Thr Ile Ser Phe Ala Gly
            340                 345                 350

Ser Gln Gly His Phe Glu Leu Asn Val Phe Lys Pro Val Met Ala Ala
        355                 360                 365

Asn Phe Leu Gln Ser Ala Gln Leu Ile Ala Asp Val Cys Ile Ser Phe
    370                 375                 380

Asp Glu His Cys Ala Thr Gly Ile Gln Pro Asn Thr Pro Arg Ile Gln
385                 390                 395                 400

His Leu Leu Asp Ser Ser Leu Met Leu Val Thr Ala Leu Asn Thr His
            405                 410                 415

Ile Gly Tyr Glu Asn Ala Ala Lys Ile Ala Lys Thr Ala His Lys Asn
            420                 425                 430

Gly Thr Thr Leu Arg Glu Glu Ala Ile Asn Leu Gly Leu Val Ser Ala
        435                 440                 445

Glu Asp Phe Asp Lys Trp Val Val Pro Ala Asp Met Val Gly Ser Leu
    450                 455                 460

Lys
465
```